US008399224B2

(12) United States Patent
Konieczny-Janda et al.

(10) Patent No.: US 8,399,224 B2
(45) Date of Patent: Mar. 19, 2013

(54) PRODUCTION OF ETHANOL FROM BARLEY AND DDGS CONTAINING REDUCED BETA-GLUCAN AND PHYTIC ACID

(75) Inventors: Gerhard Konieczny-Janda, Pattensen (DE); Mian Li, Loves Park, IL (US); Jayarama K. Shetty, Pleasanton, CA (US); Pauline J. M. Teunissen, Voorschoten (NL)

(73) Assignee: Danisco US Inc., Palo Alto, CA (US)

( * ) Notice: Subject to any disclaimer, the term of this patent is extended or adjusted under 35 U.S.C. 154(b) by 549 days.

(21) Appl. No.: 12/531,040

(22) PCT Filed: Mar. 12, 2008

(86) PCT No.: PCT/US2008/003344

§ 371 (c)(1),
(2), (4) Date: Apr. 8, 2010

(87) PCT Pub. No.: WO2008/112282

PCT Pub. Date: Sep. 18, 2008

(65) Prior Publication Data

US 2010/0196537 A1  Aug. 5, 2010

Related U.S. Application Data

(60) Provisional application No. 60/918,163, filed on Mar. 14, 2007.

(51) Int. Cl.
*C12P 19/20* (2006.01)
*C12P 7/06* (2006.01)
(52) U.S. Cl. .......................... 435/96; 435/161
(58) Field of Classification Search ............... 426/53; 435/161, 96
See application file for complete search history.

(56) References Cited

U.S. PATENT DOCUMENTS

| | | | |
|---|---|---|---|
| 4,092,434 A | 5/1978 | Yoshizumi et al. | 426/13 |
| 4,316,956 A | 2/1982 | Lutzen | 435/96 |
| 4,514,496 A | 4/1985 | Yoshizumi et al. | 435/162 |
| RE32,153 E | 5/1986 | Tamura et al. | 435/96 |
| 4,587,215 A | 5/1986 | Hirsh | 435/96 |
| 4,618,579 A | 10/1986 | Dwiggins et al. | 435/96 |
| 5,000,000 A | 3/1991 | Ingram et al. | 435/161 |
| 5,028,539 A | 7/1991 | Ingram et al. | 435/161 |
| 5,093,257 A | 3/1992 | Gray | 435/202 |
| 5,424,202 A | 6/1995 | Ingram et al. | 435/161 |
| 5,514,583 A | 5/1996 | Picataggio et al. | 435/252.3 |
| 5,554,520 A | 9/1996 | Fowler et al. | 435/161 |
| 5,763,385 A | 6/1998 | Bott et al. | 510/392 |
| 5,824,532 A | 10/1998 | Barnett et al. | 435/202 |
| 5,958,739 A | 9/1999 | Mitchinson et al. | 435/99 |
| 6,008,026 A | 12/1999 | Day | 435/96 |
| 6,093,562 A | 7/2000 | Bisgård-Frantzen et al. | 435/202 |
| 6,187,576 B1 | 2/2001 | Svendsen et al. | 435/202 |
| 6,352,851 B1 | 3/2002 | Nielsen et al. | 435/205 |
| 6,361,809 B1 | 3/2002 | Christophersen et al. | 426/52 |
| 6,867,031 B2 | 3/2005 | Bisgard-Frantzen et al. | 435/202 |
| 7,968,318 B2 * | 6/2011 | Lantero et al. | 435/99 |
| 2006/0014265 A1 | 1/2006 | Ferrari et al. | 435/204 |
| 2006/0094080 A1 | 5/2006 | Dunn-Coleman et al. | 435/69.1 |

FOREIGN PATENT DOCUMENTS

| | | |
|---|---|---|
| WO | WO 84/02921 | 8/1984 |
| WO | WO 92/00381 | 1/1992 |
| WO | WO 95/13362 | 5/1995 |
| WO | WO 96/23874 | 8/1996 |
| WO | WO 96/39528 | 12/1996 |
| WO | WO 97/41213 | 11/1997 |
| WO | WO 99/19467 | 4/1999 |
| WO | WO 99/28488 | 6/1999 |
| WO | WO 00/04136 | 1/2000 |
| WO | WO 01/62947 | 8/2001 |
| WO | WO 2004/080923 | 9/2004 |
| WO | WO 2004/081193 | 9/2004 |
| WO | WO 2004/087889 | 10/2004 |
| WO | WO 2004/111218 | 12/2004 |
| WO | WO 2005/001064 | 1/2005 |
| WO | WO 2005/052148 | 6/2005 |
| WO | WO 2007/145912 | 12/2007 |

OTHER PUBLICATIONS

Boel et al., "Glucoamylases G1 and G2 from *Aspergillus niger* are synthesized from two different but closely related mRNAs". *EMBO J.* (1984) 3(5):1097-1102.

Chen et al., "Substitution of asparagine residues in *Aspergillus awamori* glucoamylase by site-directed mutagenesis to eliminate N-glycosylation and inactivation by deamidation" *Biochem J.* (1994), 301:275-281.

Chen et al., "Identification and elimination by site-directed mutagenesis of thermolabile aspartyl bonds in *Aspergillus awamori* glucoamylase", *Prot. Eng.* (1995), 8(6):575-582.

Chen et al., "Effect of replacing helical glycine residues with alanines on reversible and irreversible stability and production of *Aspergillus awamori* glucoamylase" *Prot. Eng.* (1996) 9(6):499-505.

Hata et al., "The glucoamylase cDNA from *Aspergillus oryzae*: Its cloning, nucleotide sequence, and expression in *Saccharomyces cerevisiae*" *Agric. Biol. Chem.* (1991), 55(4):941-949.

Jensen et al., "Purification of extracellular amylolytic enzymes from the thermophilic fungus *Thermomyces lanuginosus*" *Can. J Microbiol.* (1988), 34:218-223.

Suzuki et al., Amino acid residues stabilizing a *Bacillus* α-Amylase against irreversible thermoinactivation: *J. Biol. Chem.* (1989), 264(32):18933-18938.

Swinkels, J.J.M., *Starch Conversion Technology* (1985) pp. 32-38, Eds. Van Beynum et al., Marcel Dekker Inc. New York.

(Continued)

*Primary Examiner* — Tekchand Saidha
(74) *Attorney, Agent, or Firm* — Danisco US Inc.

(57) ABSTRACT

Described herein is a method of preparing DDGS containing reduced levels of beta-glucan and phytic acid suitable for an animal feed.

15 Claims, 6 Drawing Sheets

OTHER PUBLICATIONS

Takahashi et al., "Different behavior towards raw starch of three forms of Glucoamylase from a *Rhizopus* Sp." *J. Biochem.* (1985), 98:663-671.

Taylor et al., "Some properties of a glucoamylase produced by the thermoplilic fungus *Humicola lanuginosa*", *Carbohydrate Res.* (1978), 61:301-308.

Teunissen, P., "Industrial biocatalysts for the bio-based economy." Renewable Resources and Biorefiners Conference 2006 (RRB2), [Online] Sep. 7, 2006, Retrieved from the Internet: URL:http://www.york.ac.uk/res/gcrn/presentations/Pauline%20Teunissen.pdf>, p. 6-15.

Wang, P., et al., "Comparison of Enzymatic (E-Mill) and Conventional Dry Grind Corn Processes Using a Granular Starch Hydrolyzing Enzyme." *Cereal Chemistry, American Association of Cereal Chemists*, 82: 734-738, 2005.

International Search Report and the Written Opinion of the International Searching Authority for International Application No. PCT/US08/03344 dated Aug. 1, 2008.

* cited by examiner

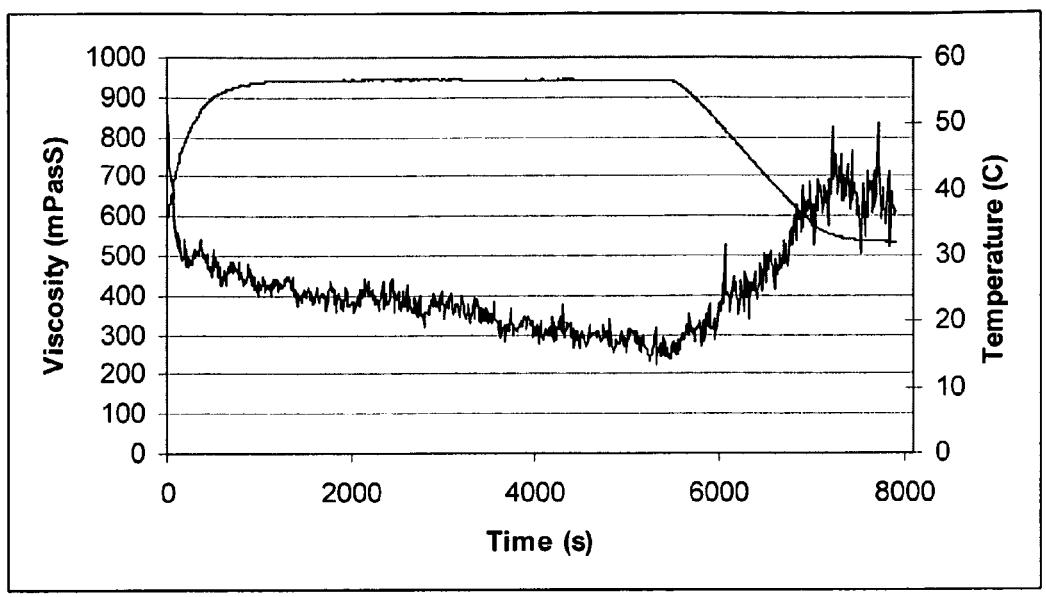
Figure 1. Effect of OPTIMASH™ BG on Barley Viscosity Reduction (30% DS, pH 3.6).

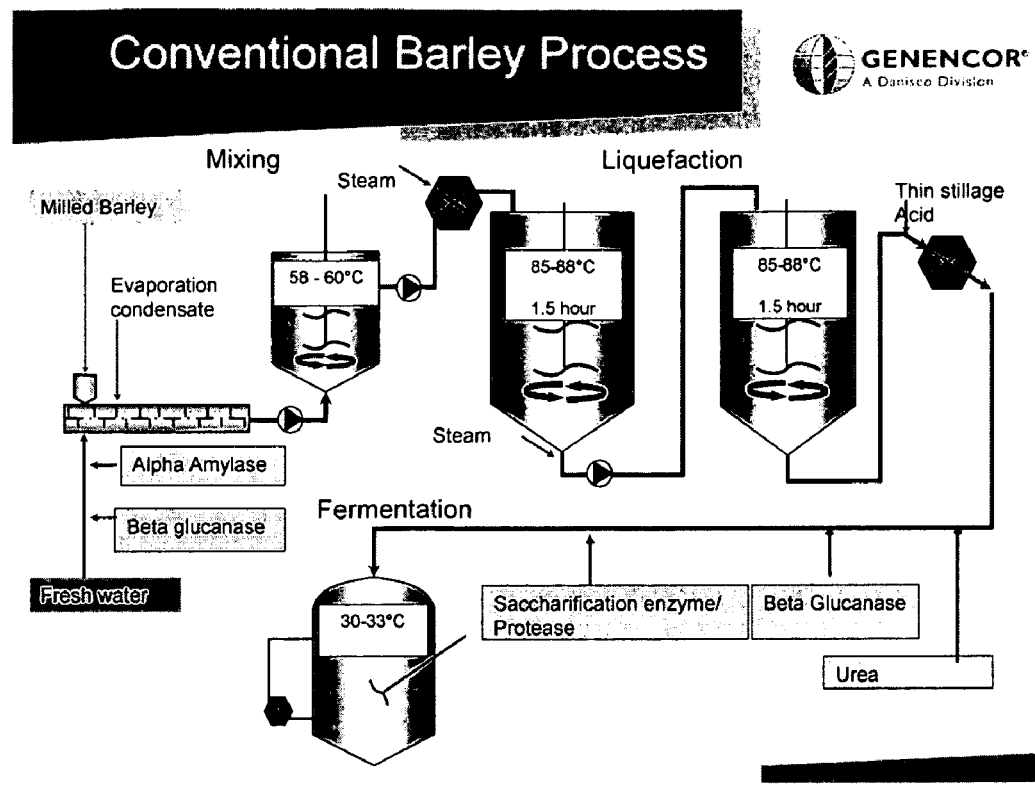
Figure 2. The Conventional Barley Dry Mill Ethanol Production Process.

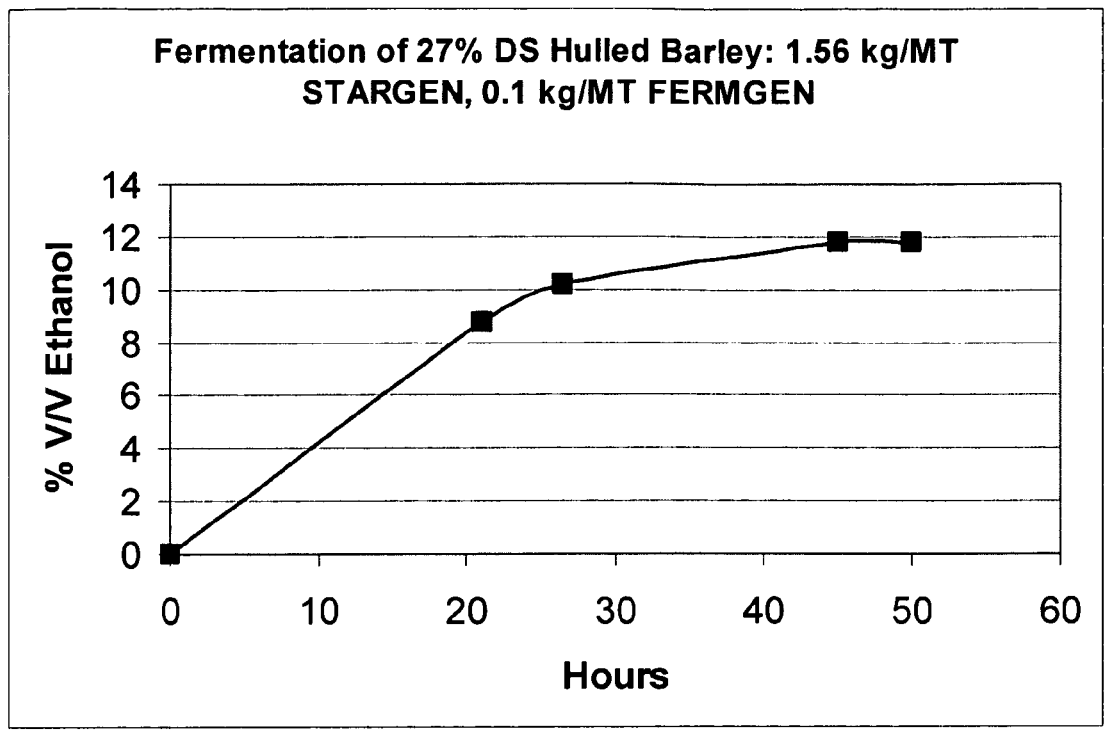
Figure 3. Production of Ethanol at 27% DS Hulled Barley

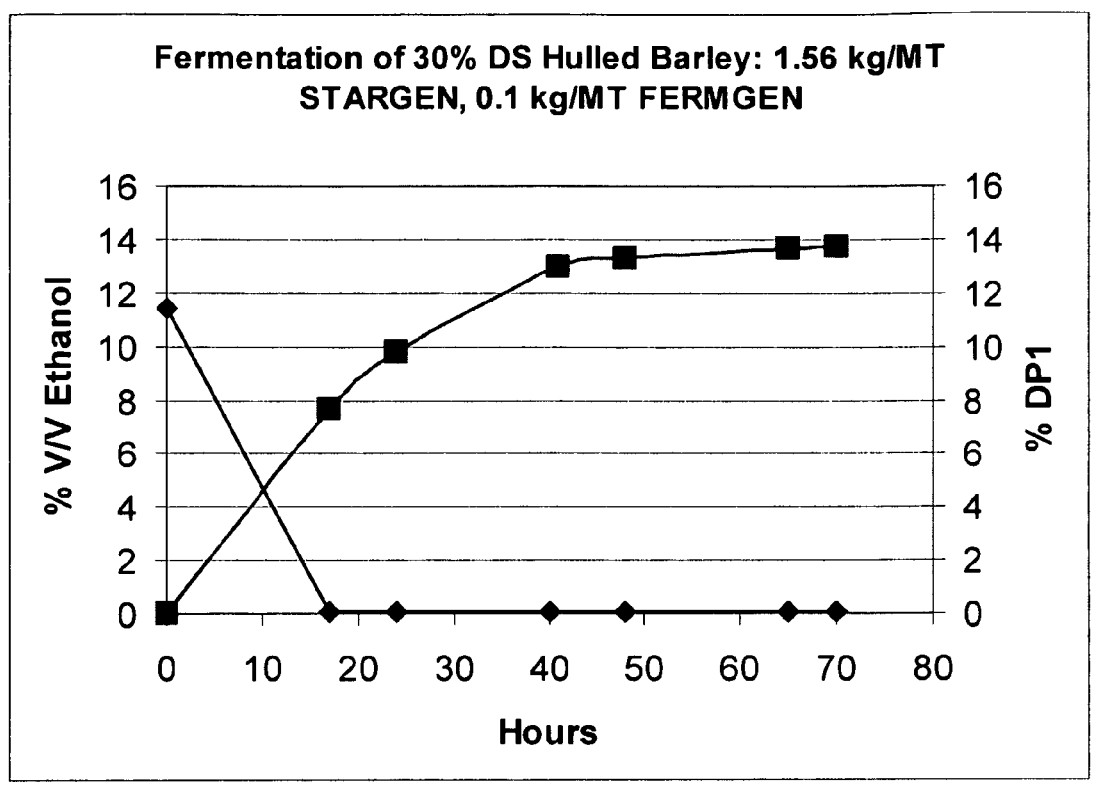
Figure 4. Production of Ethanol at 30% DS Hulled Barley

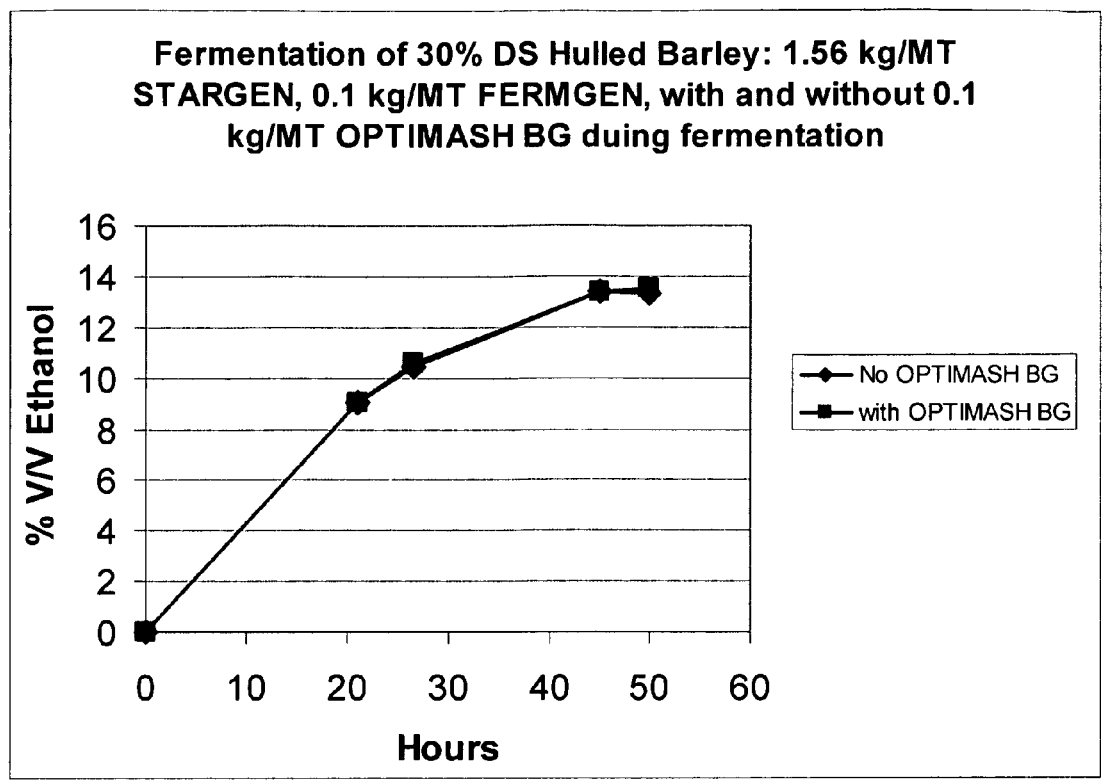
Figure 5. Effect of OPTIMASH™ BG on Ethanol Yield at 30% DS Hulled Barley

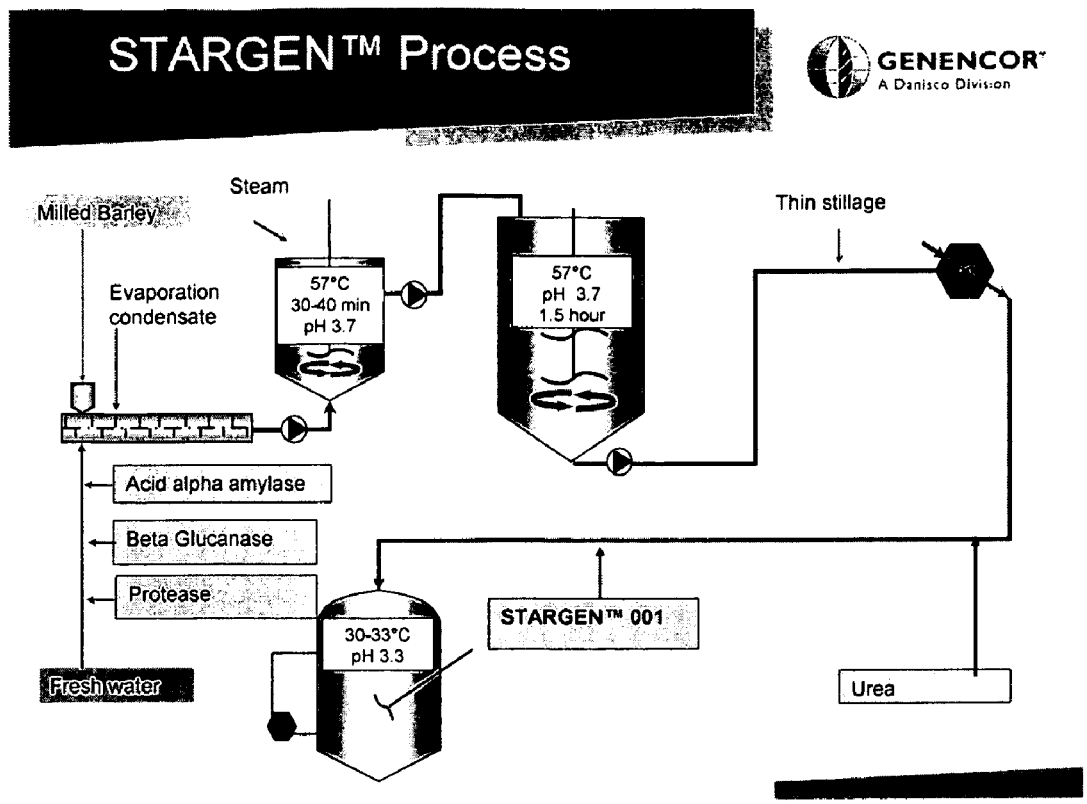
Figure 6. Low Energy Ethanol Production Process

PRODUCTION OF ETHANOL FROM BARLEY AND DDGS CONTAINING REDUCED BETA-GLUCAN AND PHYTIC ACID

This invention claims priority to U.S. Provisional application 60/918,163, filed Mar. 14, 2007, the contents of which are incorporated by reference in their entirety.

FIELD OF THE INVENTION

This invention relates to methods for starch hydrolyzing processes for obtaining DDGS containing reduced levels of beta-glucan and phytic acid suitable for an animal feed from starch in milled plant material at temperatures below the starch gelatinization temperature.

BACKGROUND OF THE INVENTION

Ethanol derived from renewable feedstock has the potential to meet one of the greatest challenges to today's society as a sustainable replacement of fossil fuels, especially in the transport sector, with reduction in greenhouse gas emission. In 2005, a record of 15.1 billion liters (4 billion gallons) of fuel ethanol was produced in the U.S. There are currently 109 ethanol plants in operation with the capacity of 19.8 billion liters (5.2 billion gallons), and 53 plants under construction will increase the capacity to 35.7 billion liters (9.4 billion gallons) (December 2006 Data). In the U.S., corn is the primary feedstock for fuel ethanol production and for example, in 2006, about 20% of the U.S. corn supply was used to make fuel ethanol to replace only 3-4% of the gasoline supply. In order to avoid the "fuel versus food" issue, an alternative to corn feedstock is needed. Among others, barley has great potential as an alternative feedstock for ethanol production, especially in the Mid-Atlantic and other states, where it is a winter crop, allowing double cropping with soybean. It is estimated that in North America, barley can provide at least one billion gallons of ethanol per year, which is about 20% of the total ethanol production in the U.S. in 2006.

However, there is no plant in the U.S. using barley as a feedstock since regular hulled barley can not be processed in a conventional corn-to-ethanol plant without modifications due to the following reasons: 1) the abrasive nature of hulled barley would damage grain handling and grinding equipment, thus increasing capital costs, 2) the low starch content (50-55%) of barley would result in lower ethanol yield compared to corn requiring barley plants to be built larger than corn plants for the same capacity, 3) the high viscosity of barley mashes due to beta-glucan, and 4) the production of a distillers dried grains with solubles (DDGS) co-product with high levels of beta-glucan that can't be used for poultry, swine, and aquaculture feeds, which limits the value of the co-product in poultry and swine production areas.

In order for a barley-to-fuel-ethanol process to be economically successful, the abovementioned technical hurdles must be overcome. The objective of this paper is to develop a barley-based STARGEN™ process for ethanol production.

BRIEF SUMMARY OF THE INVENTION

The present invention relates to a process of hydrolyzing starch from milled plant material comprising contacting milled plant material with an enzyme combination of an endogenous plant phytase, a glucoamylase and a microbial alpha-amylases at temperatures below the initial gelatinization temperature of the granular starch in the milled plant material to obtain fermentable sugars. The invention further relates to fermenting the fermentable sugars to end products in the presence of fermenting microorganisms. In another embodiment the process utilizes a beta-glucanase in the enzyme combination. In an embodiment there is provided an animal feed comprising a DDGS from yeast fermentation that is essentially free from phytic acid.

In one embodiment, the temperature below the initial gelatinization temperature is from about 25° C. and about 77° C. or about 50° C. and about 80° C. In one aspect, the end product is DDGS and the DDGS are essentially free of phytic acid. In a further aspect, the end product is DDGS and the DDGS are essentially free of β-glucan. In either case, the DDGS can be used in an animal feed. In one aspect, the milled plant material is barley, wheat or rye. The enzyme composition can also include secondary enzymes, such as a second glucoamylase, a second alpha amylase, a cellulase, a hemicellulase, a xylanase, a protease, a pullulanase, a lipase, a cutinase, a pectinase, a beta-glucanase, a cyclodextrin transglycosyltransferase, a beta-amylase, and combinations thereof. In one aspect, the pH of the slurry is between about pH 3 and about pH 7. The slurry can be held in contact with the enzyme composition for a period of about 2 hours to about 240 hours. The enzyme combination can be added to the slurry as a blend or separately. In one embodiment the milled plant material includes barley, milo, corn or combinations thereof and the contacting and fermenting steps are conducted simultaneously at a pH range of about 3.5 to about 5.5, a temperature range of about 30 about 45° C. and for a period of time of about 48 to about 90 hours, and at least about 50% of the starch is solubilized. In a further embodiment, the end-product is ethanol and the yield is greater than about 8%.

A further embodiment is a method of fermenting ethanol from milled plant material, by contacting a slurry of milled plant material with an enzyme combination of a glucoamylase and a microbial alpha-amylase at a temperature below the initial gelatinization temperature of the granular starch in the milled plant material to obtain fermentable sugars, wherein the milled plant material comprises an endogenous phytase; and fermenting the fermentable sugars to ethanol in the presence of fermenting microorganisms. The combination of enzymes can be added as a blend or separately and the combination of enzymes can also include a beta-glucanase. The fermentation can also results in the production of DDGS with reduced phytic acid and β-glucan, which can be used in animal feed.

Other objects, features and advantages of the present invention will become apparent from the following detailed description. It should be understood, however, that the detailed description and specific examples, while indicating preferred embodiments of the invention, are given by way of illustration only, since various changes and modifications within the scope and spirit of the invention will become apparent to one skilled in the art from this detailed description.

BRIEF DESCRIPTION OF THE DRAWINGS

FIG. 1 is a graph illustrating the viscosity profile of a barley slurry.

FIG. 2 illustrates the conventional barley to ethanol production process.

FIG. 3 summarizes the production of ethanol during the fermentation.

FIG. 4 summarizes the result of 30% DS hulled barley fermentation.

FIG. 5 is a graph illustrating the effect of OPTIMASH™ BG on Ethanol Yield at 30% DS Hulled Barley.

FIG. 6 summarizes the Low Energy Ethanol Production Process.

DETAILED DESCRIPTION

The invention will now be described in detail by way of reference only using the following definitions and examples. All patents and publications, including all sequences disclosed within such patents and publications, referred to herein are expressly incorporated by reference.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, N.Y. (1991) provide one of skill with a general dictionary of many of the terms used in this invention. Although any methods and materials similar or equivalent to those described herein can be used in the practice or testing of the present invention, the preferred methods and materials are described. Numeric ranges are inclusive of the numbers defining the range. Unless otherwise indicated, nucleic acids are written left to right in 5' to 3' orientation; amino acid sequences are written left to right in amino to carboxy orientation, respectively. Practitioners are particularly directed to Sambrook at al., 1989, and Ausubel F M et al., 1993, for definitions and terms of the art. It is to be understood that this invention is not limited to the particular methodology, protocols, and reagents described, as these may vary.

Numeric ranges are inclusive of the numbers defining the range.

Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention which can be had by reference to the specification as a whole. Accordingly, the terms defined immediately below are more fully defined by reference to the specification as a whole.

Although any methods and materials similar or equivalent to those described herein can be used in the practice or testing of the present invention, the preferred methods and materials are described.

Unless defined otherwise herein, all technical and scientific terms used herein have the same meaning as commonly understood by one of ordinary skill in the art to which this invention belongs.

Definitions

As used herein the term "starch" refers to any material comprised of the complex polysaccharide carbohydrates of plants, comprised of amylose and amylopectin with the formula $(C_6H_{10}O_5)_x$, wherein x can be any number.

The term "granular starch" refers to raw starch, that is starch in its natural form found in plant material (e.g. grains and tubers).

The term "fermentable sugars" refers to oligosaccharides and monosaccharides that can be converted to end products by fermentation with a fermenting microorganism.

The term "dextrins" refers to short chain polymers of glucose (e.g. 2 to 10 units).

The term "oligosaccharides" refers to any compound having 2 to 10 monosaccharide units joined in glycosidic linkages. These short chain polymers of simple sugars include dextrins.

The term "alpha-amylase (e.g., E.C. class 3.2.1.1)" refers to enzymes that catalyze the hydrolysis of alpha-1,4-glucosidic linkages.

The terms "saccharifying enzyme" and "starch hydrolyzing enzymes" refer to any enzyme that is capable of converting starch to mono- or oligosaccharides (e.g. a hexose or pentose).

The terms "granular starch hydrolyzing (GSH) enzyme" and "enzymes having granular starch hydrolyzing (GSH) activity" refer to enzymes, which have the ability to hydrolyze starch in granular form.

The term "hydrolysis of starch" refers to the cleavage of glucosidic bonds with the addition of water molecules.

The term "endogenous plant phytase" means an enzyme having phytase activity that is expressed and produced by the plant material. As used herein the endogenous plant phytase may be heterologous or homologous.

The term "microbial alpha-amylases" refers to enzymes having alpha-amylase activity which are derived from microbial sources (e.g. bacterial or fungal) and includes modified enzymes, active fragments and hybrids thereof The term "heterologous" with reference to a polynucleotide or polypeptide refers to a polynucleotide or polypeptide that does not naturally occur in a host cell. It is intended that the term encompass proteins that are encoded by naturally occurring genes, mutated genes, synthetic genes and/or overexpressed genes.

The term "homologous" with reference to a polynucleotide or protein refers to a polynucleotide or protein that occurs naturally in the host cell.

The term "glucoamylase" refers to the amyloglucosidase class of enzymes (e.g., E.C.3.2.1.3, glucoamylase, 1,4-alpha-D-glucan glucohydrolase). These are exo-acting enzymes, which release glucosyl residues from the non-reducing ends of amylose and amylopectin molecules.

The term "milled" is used herein to refer to plant material that has been reduced in size, such as by grinding, crushing, fractionating or any other means of particle size reduction.

The term "gelatinization" means solubilization of a starch molecule, generally by cooking, to form a viscous suspension.

The term "gelatinization temperature" refers to the lowest temperature at which gelatinization of a starch containing substrate begins. The exact temperature of gelatinization depends on the specific starch and may vary depending on factors such as plant species and environmental and growth conditions.

The term "below the gelatinization temperature" refers to a temperature that is less than the gelatinization temperature.

As used herein the term "dry solids content (DS)" refers to the total solids of a milled grain in % on a dry weight basis including moisture.

The term "slurry" refers to an aqueous mixture comprising insoluble solids, (e.g. granular starch).

The term "mash" refers to a mixture of a fermentable substrate in liquid used in the production of a fermented product and is used to refer to any stage of the fermentation from the initial mixing of the fermentable substrate with one or more starch hydrolyzing enzymes and fermenting organisms through the completion of the fermentation run.

The term "fermentation" refers to the enzymatic and anaerobic breakdown of organic substances by microorganisms to produce simpler organic compounds. While fermentation occurs under anaerobic conditions it is not intended that the term be solely limited to strict anaerobic conditions, as fermentation also occurs in the presence of oxygen.

The phrase "simultaneous saccharification and fermentation (SSF)" refers to a process in the production of end products in which a fermenting organism, such as an ethanol producing microorganism, and at least one enzyme, such as a saccharifying enzyme are combined in the same process step in the same vessel.

The term "saccharification" refers to enzymatic conversion of a directly unusable polysaccharide to a mono- or oligosaccharide for fermentative conversion to an end product.

The term "end product" refers to any carbon-source derived product which is enzymatically converted from a fermentable substrate. In some preferred embodiments, the end product is an alcohol, such as ethanol.

As used herein the term "fermenting organism" refers to any microorganism or cell, which is suitable for use in fermentation for directly or indirectly producing an end product.

As used herein the term "ethanol producer" or ethanol producing microorganism" refers to a fermenting organism that is capable of producing ethanol from a mono- or oligosaccharide.

The terms "recovered", "isolated", and "separated" as used herein refer to a protein, cell, nucleic acid or amino acid that is removed from at least one component with which it is naturally associated.

The term "derived" encompasses the terms "originated from", "obtained" or "obtainable from", and "isolated from" and in some embodiments as used herein means that a polypeptide encoded by the nucleotide sequence is produced from a cell in which the nucleotide is naturally present or in which the nucleotide has been inserted.

The term "enzymatic conversion" in general refers to the modification of a substrate by enzyme action.

The term "yield" refers to the amount of end product produced using the methods of the present invention. In some embodiments, the term refers to the volume of the end product, and in other embodiments, the term refers to the concentration of the end product.

As used herein the term "enzyme unit" refers to the amount of enzyme that produces 1 micromole of product per minute under the specified conditions of the assay. For example, in one embodiment, the term "glucoamylase activity unit" (GAU) is defined as the amount of enzyme required to produce 1 g of glucose per hour from soluble starch substrate (4% DS) under assay conditions of 60° C. and pH 4.2. In another embodiment, one unit of enzyme activity for a "soluble starch unit (SSU)" is equivalent to the reducing power of 1 mg of glucose released per minute at the specific incubation conditions and is based on the degree of hydrolysis of soluble potato starch substrate (4% DS) by an aliquot of the enzyme sample at pH 4.5, 50° C.

As used herein the term "comprising" and its cognates are used in their inclusive sense; that is, equivalent to the term "including" and its corresponding cognates.

"A", "an" and "the" include plural references unless the context clearly dictates otherwise.

EMBODIMENTS OF THE INVENTION

Milled Plant Material-

Plant material comprising granular starch may be obtained from but not limited to wheat, corn, rye, sorghum (milo), rice, millet, barley, triticale, cassaya (tapioca), potato, sweet potato, sugar beets, sugarcane, and legumes such as soybean and peas. Preferred plant material includes corn, barley, wheat, rice, milo and combinations thereof. Plant material may include hybrid varieties and genetically modified varieties (e.g. transgenic corn, barley or soybeans comprising heterologous genes). Any part of the plant may be used to as plant material including but not limited to plant parts such as leaves, stems, hulls, husks, tubers, cobs, grains and the like. In one embodiment, whole grain may be used as a source of granular starch. Preferred whole grains include corn, wheat, rye, barley, sorghum and combinations thereof.

Preferably the whole grain is reduced in size by means known in the art including milling (e.g. hammer milling or roller milling); emulsion technology; rotary pulsation; fractionation and the like. In some embodiments, the plant material is ground so that at least 70% will pass through a sieve having a 0.5 mm screen. In some embodiments, at least 90% of the ground plant material will pass through a sieve having a 0.5 mm screen.

In other embodiments, the plant material is fractionated cereal grain, which includes fiber, endosperm and/or germ components. In some embodiments certain fractions will be used in the starch hydrolysis process of the invention. Methods for fractionating plant material such as corn, barley and wheat are known in the art.

Plant Phytases-

In an embodiment according to the invention, an endogenous plant phytase enzyme participates in the degradation of phytic acid from a milled plant material.

At temperatures conducted in the present process, it is believed that the endogenous plant phytases are not inactivated and may also contribute to the degradation of phytic acid.

Glucoamylases-

In a preferred embodiment of the invention, the process includes contacting the milled plant material with a combination of an exogenous plant alpha-amylase and a glucoamylase.

Glucoamylases (E.C. 3.2.1.3.) may be derived from the heterologous or endogenous protein expression of bacteria, plants and fungi sources. Preferred glucoamylases useful in the invention are produced by several strains of filamentous fungi and yeast. In particular, glucoamylases secreted from strains of *Aspergillus* and *Trichoderma* are commercially important. Suitable glucoamylases include naturally occurring wild-type glucoamylases as well as variant and genetically engineered mutant glucoamylases. The following glucoamylases are nonlimiting examples of glucoamylases that may be used in the process encompassed by the invention. *Aspergillus niger* G1 and G2 glucoamylase (Boel et al., (1984) EMBO J. 3:1097-1102; WO 92/00381, WO 00/04136 and U.S. Pat. No. 6,352,851); *Aspergillus awamori* glucoamylases (WO 84/02921); *Aspergillus oryzae* glucoamylases (Hata et al., (1991) Agric. Biol. Chem. 55:941-949) and *Aspergillus shirousami*. (See Chen et al., (1996) Prot. Eng. 9:499-505; Chen et al. (1995) Prot. Eng. 8:575-582; and Chen et al., (1994) Biochem J. 302:275-281).

Glucoamylases are also obtained from strains of Talaromyces such as those derived from *T. emersonii, T. leycettanus, T. duponti* and *T. thermophilus* (WO 99/28488; USP No. RE: 32,153; U.S. Pat. No. 4,587,215); strains of *Trichoderma*, such as *T. reesei* and particularly glucoamylases having at least 80%, 85%, 90% and 95% sequence identity to SEQ ID NO: 4 disclosed in US Pat. Pub. No. 2006-0094080; strains of *Rhizopus*, such as *R. niveus* and *R. oryzae*; strains of *Mucor* and strains of *Humicola*, such as *H. grisea* (See, Boel et al., (1984) EMBO J. 3:1097-1102; WO 92/00381; WO 00/04136; Chen et al., (1996) Prot. Eng. 9:499-505; Taylor et al., (1978)

Carbohydrate Res. 61:301-308; USP. 4,514,496; U.S. Pat. No. 4,092,434; U.S. Pat. No. 4,618,579; Jensen et al., (1988) Can. J. Microbiol. 34:218-223 and SEQ ID NO: 3 of WO 2005/052148). In some embodiments, the glucoamylase will have at least 85%, 90%, 92%, 94%, 95%, 96%, 97%, 98% and 99% sequence identity to the amino acid sequence of SEQ ID NO: 3 of WO 05/052148.

Other glucoamylases useful in the present invention include those obtained from *Athelia rolfsii* and variants thereof (WO 04/111218).

Enzymes having glucoamylase activity used commercially are produced for example, from *Aspergillus niger* (trade name DISTILLASE, OPTIDEX L-400 and G ZYME G990 4X from Genencor International Inc.) or *Rhizopus* species (trade name CU.CONC from Shin Nihon Chemicals, Japan). Also the commercial digestive enzyme, trade name GLUCZYME from Amano Pharmaceuticals, Japan (Takahashi et al., (1985) J. Biochem. 98:663-671). Additional enzymes include three forms of glucoamylase (E.C.3.2.1.3) of a *Rhizopus* sp., namely "Gluc1" (MW 74,000), "Gluc2" (MW 58,600) and "Gluc3" (MW 61,400). Also the enzyme preparation GC480 (Genencor International Inc.) finds use in the invention.

Microbially Derived Alpha-amylase-

In another preferred embodiment of the invention, the process includes contacting milled plant material with a combination of an exogenous plant alpha-amylase, a glucoamylase and a microbially derived alpha-amylase.

Any suitable alpha-amylase may be used as a microbial alpha-amylase in the invention. In some embodiments, the alpha-amylase is derived from a bacterial strain and in other embodiments the alpha-amylase is derived from a fungal strain. In further embodiments, the preferred alpha-amylase is a bacterial alpha-amylase. In other embodiments, the alpha-amylase is an acid stable alpha-amylase. Suitable alpha-amylases may be naturally occurring as well as recombinant (hybrid and variants) and mutant alpha-amylases (WO 99/19467 and WO 97/41213). In some preferred embodiments, the alpha-amylase is derived from a *Bacillus* species. Preferred *Bacillus* species include *B. subtilis, B. stearothermophilus, B. lentus, B. licheniformis, B. coagulans,* and *B. amyloliquefaciens* (U.S. Pat. Nos. 5,093,257; 5,763,385; 5,824,532; 5,958,739; 6,008,026, 6,361,809; 6,867,031; WO 96/23874; WO 96/39528 and WO 05/001064). Particularly preferred alpha-amylases are derived from *Bacillus* strains *B. stearothermophilus, B. amyloliquefaciens* and *B. licheniformis* ((U.S. Pat. Nos. 6,187,576; 6,093,562; 5,958,739; US 2006/0014265 and WO 99/19467). Such alpha-amylases include wild type, hybrid and variant alpha-amylase enzymes. See Suzuki et al., (1989) J. Biol. Chem. 264:18933-18938 and US 2006/0014265, particularly SEQ ID NOs: 3, 4 and 16. Reference is also made to strains having American Type Culture Collection (ATCC) numbers—ATCC 39709; ATCC 11945; ATCC 6598; ATCC 6634; ATCC 8480; ATCC 9945A and NCIB 8059.

In addition to the bacterial alpha-amylases, fungal alpha-amylases are contemplated for use in the processes of the invention. Suitable fungal alpha-amylases are derived from filamentous fungal strains such as *Aspergillus*, such as *A. oryzae* and *A. niger* (e.g. FUNGAMYL and CLARASE L), and *Trichoderma, Rhizopus, Mucor,* and *Penicillium*.

Commercially available alpha-amylases contemplated for use in the methods of the invention include; SPEZYME AA; SPEZYME FRED; SPEZYME ETHYL; GZYME G997; CLARASE L (Genencor International Inc.); TERMAMYL 120-L, LC, SC and SUPRA (Novozymes Biotech); LIQUOZYME X and SAN SUPER (Novozymes A/S) and ULTRA THIN (/Valley Research).

Beta-glucanases-

In another preferred embodiment of the invention, the process includes contacting milled plant material with a combination of an exogenous plant alpha-amylase, a glucoamylase and a beta-glucanase. The type of beta-glucanase is not critical, but preferably, the beta-glucanase is capable of hydrolyzing beta-glucan. Thus, any beta-glucanases that are known or are developed that have this property can be used in the methods of the invention.

Beta-glucanase (endo-cellulase—enzyme classification EC 3.2.1.4) also called endoglucanase I, II, and III, is an enzyme that will attack the cellulose fiber to liberate smaller fragments of cellulose which is further attacked by exo-cellulase to liberate glucose. □-glucanases can also be used in the methods according to the invention. Commercial beta-glucanases useful in the methods of the invention include OPTIMASH BG and OPTIMASH TBG (Danisco, US, Inc. Genencor Division).

Fermenting Organisms-

Examples of fermenting organisms are ethanologenic microorganisms or ethanol producing microorganisms such as ethanologenic bacteria which express alcohol dehydrogenase and pyruvate dehydrogenase and which can be obtained from *Zymomonas moblis* (See e.g. U.S. Pat. Nos. 5,000,000; 5,028,539, 5,424,202; 5,514,583 and 5,554,520). In additional embodiments, the ethanologenic microorganisms express xylose reductase and xylitol dehydrogenase, enzymes that convert xylose to xylulose. In further embodiments, xylose isomerase is used to convert xylose to xylulose. In particularly preferred embodiments, a microorganism capable of fermenting both pentoses and hexoses to ethanol are utilized. For example, in some embodiments the microorganism may be a natural or nongenetically engineered microorganism or in other embodiments the microorganism may be a recombinant microorganism.

In some embodiments, the preferred fermenting microorganisms include bacterial strains from *Bacillus, Lactobacillus, E. coli, Erwinia, Pantoea* (e.g., *P. citrea*), *Pseudomonas* and *Klebsiella* (e.g. *K. oxytoca*). (See e.g. U.S. Pat. Nos. 5,028,539, 5,424,202 and WO 95/13362). The fermenting microorganism used in the fermenting step will depend on the end product to be produced.

In further preferred embodiments, the ethanol-producing microorganism is a fungal microorganism, such as a yeast and specifically *Saccharomyces* such as strains of *S. cerevisiae* (U.S. Pat. No. 4,316,956). A variety of *S. cerevisiae* are commercially available and these include but are not limited to FALI (Fleischmann's Yeast), SUPERSTART (Alltech), FERMIOL (DSM Specialties), RED STAR (Lesaffre) and Angel alcohol yeast (Angel Yeast Company, China).

Secondary Enzymes-

While embodiments of the invention include endogenous plant phytases, microbially derived glucoamylases and microbially derived alpha-amylases, further enzymes may be included in the contacting step and/or the fermenting step along with the fermenting microorganism and other components. The additional enzymes include without limitation, cellulases, hemicellulases, xylanase, proteases, pullulanases, lipases, cutinases, pectinases, beta-glucanases, cyclodextrin transglycosyltransferases, beta-amylases and combinations thereof. The use of beta-glucanases may assist in decreasing the mash viscosity.

Process Steps-

In some embodiments the milled plant material comprising granular starch is mixed with an aqueous solution to obtain a slurry. The slurry may have a DS of between about 5-about 60%; 10-50%; 15-45%; 15-30%; 20-45%; 20-30% and also 25-40%. The slurry is contacted with an exogenous plant alpha-amylase, a glucoamylase and optionally a microbial alpha-amylase under suitable conditions to produce fermentable sugars.

The pH range of the contacting step is between about pH 3.0 to about pH 7.0; also between about pH 3.5 to about 6.5; also between about pH 4.0 to about 6.0 and further between about pH 4.0 to about 5.5. The slurry is held in contact with the enzymes at a temperature below the starch gelatinization temperature of the granular starch in the milled plant material. In some embodiments, the temperature is held between about 25° C. and about 75° C.; in other embodiments, the temperature is held between about 30° C. and about 70° C.; between about 30° C. and about 65° C.; between about 40° C. and about 65° C.; between about 55° C. and about 70° C., between about 60° C. and about 65° C.; between about 55° C. and about 65° C., between about 55° C. and about 78° C., and between about 55° C. and about 68° C. In further embodiments, the temperature is at least about 25° C. 30° C., 35° C., 40° C., 45° C., 48° C., 50° C., 53° C., 55° C., 58° C., 60° C., 63° C., 65° C. and 68° C. In other embodiments, the temperature is not greater than about 65° C., 68° C., 70° C., 73° C., 75° C. and 80° C.

The initial starch gelatinization temperature ranges for a number of granular starches which may be used in accordance with the processes herein include barley (52° C. to 59° C.), wheat (58° C. to 64° C.), rye (57° C. to 70° C.), corn (62° C. to 72° C.), high amylose corn (67° C. to 80° C.), rice (68° C. to 77° C.), sorghum (68° C. to 77° C.), potato (58° C. to 68° C.), tapioca (59° C. to 69° C.) and sweet potato (58° C. to 72° C.). (J. J. M. Swinkels pg 32-38 in Starch Conversion Technology, Eds Van Beynum et al., (1985) Marcel Dekker Inc. New York and The Alcohol Textbook 3$^{rd}$ ED. A Reference for the Beverage, Fuel and Industrial Alcohol Industries, Eds Jacques et al., (1999) Nottingham University Press, UK).

In the contacting step, the slurry may be held in contact with the enzymes for a period of about 2 hrs to about 240 hrs; also for about 2 hrs to about 120 hrs; also for about 5 hrs to about 90 hrs; for about 5 hrs to about 72 hrs; and about 5 hrs to about 48 hrs.

The effective concentration of the alpha-amylase used in the contacting step will vary according to the specific process conditions and granular starch used. However, in general the amount of alpha-amylase used will be in the range of about 0.001 to about 50 AAU/g DS, about 0.01 to about 30 AAU/g DS, about 0.01 to about 10 AAU/g DS and also about 0.05 to about 5.0 AAU/g DS.

In some embodiments, the effective dose of an alpha-amylase in the contacting step and/or fermentation step will be about 0.01 to about 25 SSU/g DS; also about 0.01 to about 15 SSU/g DS; also about 0.05 to about 10 SSU/g DS; also about 0.1 to about 10 SSU/g DS; also about 0.1 to about 10 SSU/g DS and about 0.5 to about 5 SSU/g DS.

In some embodiments, the effective dose of a glucoamylase for the contacting step and/or the fermentation step will be in the range of about 0.01 to about 20 GAU/g DS; also about 0.01 to about 15 GAU/g DS; also about 0.05 to about 10 GAU/g DS; also about 0.1 to about 10 GAU/g DS and even about 0.5 to about 5 GAU/g DS.

During the contacting step between about 20-about 95% of the granular starch is solubilized to produce fermentable sugars such as oligosaccharides. In some embodiments greater than about 40%, greater than about 50%, greater than about 60%, greater than about 70%, greater than about 80%, and greater than about 90% of the starch is solubilized. In some embodiments the solubilized starch comprises greater than about 10%, 15%, 20%, 25%, 30%, 35%, 40%, 45%, 50%, 55%, 60%, 65%, 70%, 75% and 80% glucose.

In some embodiments, the mash comprising fermentable sugars may be further converted to end products such as high fructose sugars. In other embodiments the fermentable sugars are subjected to fermentation with fermenting microorganisms. The contacting step and the fermenting step may be preformed simultaneously in the same reaction vessel or sequentially. In general, fermentation processes are described in The Alcohol Textbook 3$^{rd}$ ED, A Reference for the Beverage, Fuel and Industrial Alcohol Industries, Eds Jacques et al., (1999) Nottingham University Press, UK.

In some preferred embodiments, the mash is fermented with a yeast at temperatures in the range of about 15 to about 40° C., about 20 to about 38° C., and also about 25 to about 35° C.; at a pH range of about pH 3.0 to about 6.5; also about pH 3.0 to about 6.0; about pH 3.0 to about 5.5, about pH 3.5 to about 5.0 and also about pH 3.5 to about 4.5 for a period of time of about 5 hrs to about 120 hours, preferably about 12 to about 120 and more preferably from about 24 to about 90 hours to produce an alcohol product, preferably ethanol.

Yeast cells are generally supplied in amounts of $10^4$ to $10^{12}$, and preferably from $10^7$ to $10^{10}$ viable yeast count per ml of fermentation broth. The fermentation will include in addition to a fermenting microorganisms (e.g. yeast) nutrients, optionally acid and additional enzymes. In some embodiments, in addition to the raw materials described above, fermentation media will contain supplements including but not limited to vitamins (e.g. biotin, folic acid, nicotinic acid, riboflavin), cofactors, and macro and micro-nutrients and salts (e.g. $(NH_4)_2SO_4$; $K_2HPO_4$; $NaCl$; $MgSO_4$; $H_3BO_3$; $ZnCl_2$; and $CaCl_2$).

In some preferred embodiments, the milled plant material includes barley, milo, corn and combinations thereof, and the contacting and fermenting steps are conducted simultaneously at a pH range of 3.5 to 5.5, a temperature range of 30-45° C., and for a period of time of 48 to 90 hrs, wherein at least 50% of the starch is solubilized.

Recovery of Alcohol and Other End Products-

The preferred end product of the instant fermentation process is an alcohol product, preferably ethanol. The end product produced according to the process may be separated and/or purified from the fermentation media. Methods for separation and purification are known, for example by subjecting the media to extraction, distillation and column chromatography. In some embodiments, the end product is identified directly by submitting the media to high-pressure liquid chromatography (HPLC) analysis.

In further embodiments, the mash may be separated by for example centrifugation into the liquid phase and solids phase and end products such as alcohol and solids recovered. The alcohol may be recovered by means such as distillation and molecular sieve dehydration or ultra filtration.

In some embodiments, the yield of ethanol will be greater than about 8%, 10%, 12%, 14%, 16% and 18% by volume. The ethanol obtained according to process of the invention may be used as a fuel ethanol, potable ethanol or industrial ethanol.

In further embodiments, the end product may include the fermentation co-products such as distillers dried grains (DDG) and distiller's dried grain plus solubles (DDGS), which may be used as an animal feed.

In further embodiments, by use of appropriate fermenting microorganisms as known in the art, the fermentation end product may include without limitation glycerol, 1,3-propanediol, gluconate, 2-keto-D-gluconate, 2,5-diketo-D-gluconate, 2-keto-L-gulonic acid, succinic acid, lactic acid, amino acids and derivatives thereof. More specifically when lactic acid is the desired end product, a *Lactobacillus* sp. (*L. casei*) may be used; when glycerol or 1,3-propanediol are the desired end-products *E. coli* may be used; and when 2-keto-D-gluconate, 2,5-diketo-D-gluconate, and 2-keto-L-gulonic acid are the desired end products, *Pantoea citrea* may be used as the fermenting microorganism. The above enumerated list are only examples and one skilled in the art will be aware of a number of fermenting microorganisms that may be appropriately used to obtain a desired end product.

In the experimental disclosure which follows, the following abbreviations apply: eq (equivalents); M (Molar); µM (micromolar); N (Normal); mol (moles); mmol (millimoles); µmol (micromoles); nmol (nanomoles); g (grams); mg (milligrams); kg (kilograms); µg (micrograms); L (liters); ml (milliliters); µl (microliters); cm (centimeters); mm (millimeters); µm (micrometers); nm (nanometers); ° C. (degrees Centigrade); h (hours); min (minutes); sec (seconds); msec (milliseconds); Ci (Curies) mCi (milliCuries); µCi (microCuries); TLC (thin layer achromatography); Ts (tosyl); Bn (benzyl); Ph (phenyl); Ms (mesyl); Et (ethyl), Me (methyl).

EXAMPLES

The present invention is described in further detail in the following examples which are not in any way intended to limit the scope of the invention as claimed. The attached Figures are meant to be considered as integral parts of the specification and description of the invention. All references cited are herein specifically incorporated by reference for all that is described therein. The following examples are offered to illustrate, but not to limit the claimed invention.

In the following examples the materials used were: Hulled Barley (Thoroughbred Lot 1504-1, grown in 2005) was obtained from the Virginia Foundation Seed Center Farm at Mt. Holly, Va. Characterization of the hulled barley was determined by USDA Eastern Regional Research Center (ERRC) and summarized in the following Table (on a dry basis).

TABLE 1

Chemical and physical characterization of hulled barley

| | |
|---|---|
| Moisture % (ground kernels) | 7.85 |
| Ash % | 2.32 |
| Oil % | 1.92 |
| Starch % | 59.89 |
| Protein % | 7.60 |
| Beta-glucan % | 3.90 |
| Acid Detergent Fiber (% ADF) | 5.47 |
| Neutral Detergent Fiber (% NDF) | 17.22 |
| Crude Fiber (% CF) | 4.66 |
| lbs/bu | 52.94 |

Commercial *Trichoderma reesei* OPTIMASH™ BG (beta-glucanase), acid stable alpha amylase, STARGEN™ 001 (granular starch hydrolyzing enzymes), FERMGEN™ (protease) were from Genencor Division, A Danisco Company.

Example 1

This example illustrates the Effect of Beta-Glucanase on Viscosity Reduction

A particular problem using barley for ethanol production is that viscosity of the barley mashes would become a major issue at higher solid levels due to beta-glucan content. It is the high viscosity of barley mash that makes agitation, liquefaction, saccharification, and fermentation technically difficult and adds significantly to operating costs. Therefore, for the dry grind fermentation processing of barley, non-starch hydrolyzing enzymes, such as cellulase and beta-glucanase, are required for reduction of viscosity to acceptable levels. The beta-glucanase tested was OPTIMASH™ BG, which contains a combination of enzymes which effectively modify and digest non-starch carbohydrates, the structural material of plant cell walls.

Barley mash was made at 30% DS and adjusted to pH 3.6. After mixing and adjusting the pH, the slurry was transferred to the measuring tube of the Haake Viscotester VT550. The Viscotester was preheated to 57° C. OPTIMASH™ BG was directly added at the start of viscosity measurement. The Viscotester was started and allowed to run for 90 minutes at a temperature of 57° C. After 90 minutes, the temperature was lowered to 32° C. (fermentation temperature) and the Viscotester was kept running for an additional 30 minutes. FIG. 1 shows the viscosity profile of the slurry. The results indicate that OPTIMASH™ BG helped reduce viscosity of barley mash. In addition, the control was run with no OPTIMASH™ BG. The Viscotester couldn't reach the 57° C. test temperature, as the rotor stopped at 54° C., indicating the control mash was too viscous for measurement.

Treating the barley slurries with OPTIMASH™ BG can effectively reduce the viscosity problems associated with slurries containing high levels of beta-glucan. The reduction in viscosity can resolve problem with pumping and processing the mash.

Example 2

The following example details the use of Granular Starch Hydrolyzing Enzyme (GSHE) for Barley Fermentation.

In a typical dry grind grain ethanol process, the entire grain is first milled and then processed without separating out the various components of the grain. The milled grain is slurried with water. After an alpha amylase and beta-glucanase are added, the slurry is cooked at 58-60° C. to reduce the viscosity of the barley mash. Then the slurry is cooked at high temperature (85-88° C.) to gelatinize and liquefy the starch in a process called liquefaction. The high temperatures also reduce microbial contaminant levels in the resulting mash. After liquefaction, the mash is cooled and a secondary enzyme (glucoamylase) is added to convert the liquefied starch to fermentable sugars (glucose, also known as dextrose) in a process called saccharification. Yeast is added to the mash to ferment the sugars to ethanol and carbon dioxide. This process is called fermentation. FIG. 2 illustrates the conventional barley to ethanol production process. In general, this is an energy-intensive process that requires the addition of heat energy to starch granule slurries until the gelatinization temperature of the starch is exceeded.

At Genencor, we have developed the STARGEN™ line of enzyme products, granular starch hydrolyzing enzymes used in a low-energy process that effectively hydrolyzes starch in the granular (un-cooked) state. The new technology has the potential to eliminate the need for high-energy processing of starch and provide more cost-effective production of glucose for conversion to ethanol and other bioproducts and biomaterials. Because of the ability to conduct several of the grain processing steps (liquefaction, saccharification, and fermentation) simultaneously in the same vessel, the process also has the ability to lower equipment and capital costs in an ethanol facility. The STARGEN™ line of products includes blends of enzymes that have synergistic activities on granular starch. The blend includes an alpha amylase and a glucoamylase that can "drill" holes in the starch granules or "peel" the starch granules depending on the substrates. In this paper, we applied this new enzyme technology to barley fermentation.

27-30% DS ground hulled barley was prepared and pH was adjusted to 3.6 using sulfuric acid. OPTIMASHT™ BG was added to the slurry at a dosage equivalent to 0.2 kg per ton of grain (kg/ton) and acid stable alpha amylase at 0.13 kg/ton (t=57° C., pH=3.6) (See Table 2—Viscosity Reduction Conditions). The slurry was then placed in a 57° C. water bath for 1.5 hours. During the incubation the slurry was gently stirred with an overhead mixer. Barley starch was not gelatinized at 57° C., which is below the gelatinization temperature for barley. Viscosity problems were not observed in this step. Table 3 shows the result of HPLC profile, supernatant Brix and % solubilization of hulled barley. The HPLC composition showed 19.78% glucose, 20.90% DP2, 8.80% DP3, and 50.53% higher sugars. 28.4% of the barley starch was solubilized.

TABLE 2

Viscosity Reduction Conditions

| Enzyme | Dose | |
| --- | --- | --- |
| Acid stable alpha amylase | kg/ton | 0.13 |
| OPTIMASH ™ BG | kg/ton | 0.2 |

TABLE 3

HPLC profile, Brix and % solubilization of Hulled Barley Mash

| DS % | % DP1 | % DP2 | % DP3 | % HS | Brix | % solubilization |
| --- | --- | --- | --- | --- | --- | --- |
| 27 | 19.78 | 20.90 | 8.80 | 50.53 | 6.5 | 28.4 |
| 30 | 11.43 | 15.00 | 12.36 | 61.21 | 7.0 | 27.1 |

Simultaneous saccharification and fermentation (SSF) was carried out with addition of 400 ppm urea. At each dosage, fermentations were run in triplicate. The enzymes added were 1.56 kg/ton STARGEN™ 001, and 0.1 kg/ton FERMGENT™. At various time intervals samples of the beer were removed for HPLC analysis.

FIG. 3 summarizes the production of ethanol during the fermentation. The results show that fermentation finished in 45-50 hours producing 11.80% v/v ethanol. In another experiment, 30% DS hulled barley was employed. Again, there is no viscosity issue. FIG. 4 summarizes the result of 30% DS hulled barley fermentation. Particularly, the fact that glucose concentration stays very low (0.048-0.067%) during the fermentation (see Table 4 HPLC results during fermentation with STARGEN™ 001) would result in enhancing the active yeast population and limiting the growth of undesirable contaminating microorganisms. Direct conversion of the granular starch using the STARGEN™ enzymes allows very high-gravity fermentation of very low-soluble solids. This significantly reduces the osmotic stress on the yeast and can result in higher concentrations of ethanol and higher throughput in the final distillation step. The lower osmotic pressure exerted also results in the yeast producing lower level of wasteful products like glycerol, and reduced glycerol production enables more glucose to be converted to ethanol.

TABLE 4

HPLC results during fermentation with STARGEN ™ 001

| Hours | % W/V DP > 3 | % W/V DP3 | % W/V DP2 | % W/V Glucose | % W/V Lactic Acid | % W/V Glycerol | % V/V Ethanol |
| --- | --- | --- | --- | --- | --- | --- | --- |
| 17 | 2.209 | 0.344 | 0.588 | 0.067 | 0.044 | 0.444 | 7.65 |
| 24 | 2.038 | 0.301 | 0.587 | 0.066 | 0.045 | 0.551 | 9.67 |
| 40 | 1.850 | 0.239 | 0.571 | 0.067 | 0.057 | 0.705 | 13.08 |
| 48 | 1.844 | 0.236 | 0.595 | 0.065 | 0.053 | 0.744 | 13.28 |
| 65 | 2.080 | 0.000 | 0.572 | 0.052 | 0.039 | 0.726 | 13.79 |
| 70 | 2.062 | 0.000 | 0.559 | 0.048 | 0.019 | 0.733 | 13.75 |

In addition to STARGENT™ and FERMGENT™ at the above dosage, the addition of OPTIMASH™ BG at 0.1 kg/ton during the fermentation has no effect on ethanol yield as shown in FIG. 5. However, adding OPTIMASH™ BG in the SSF step may have the benefit of further reducing the viscosity of the mash, thus improving the downstream processing.

In general, the STARGEN™ enzyme technology (FIG. 6), capable of hydrolyzing insoluble granular (uncooked) starch into fermentable sugars by enabling depolymerization of starch to glucose in a SSF process, offers several potential benefits for ethanol production. The above results clearly demonstrate the elimination of jet cooking with STARGEN™ enzyme, which would result in significant energy savings. In addition, STARGEN™ process resulted in more ethanol yield than that of conventional process as seen in Table 5 (14.87% vs. 14.60%) (Comparison of Hulled Barley Fermentation). For STARGEN™ process, 0.538 kg Ethanol/kg Starch can be obtained, corresponding to fermentation efficiency being 95.8%.

TABLE 5

Comparison of Hulled Barley Fermentation

| | EtOH % V/V | Standard Deviation % |
| --- | --- | --- |
| Conventional Process | 14.60 | 0.08 |
| STARGEN ™ Process | 14.87 | 0.06 |

Example 3

This example describes the Characterization of DDGS in terms of Residual Starch, Beta-Glucan, and Phytic Acid.

After the fermentation the beer was dried in a forced air oven to obtain DDGS. The residual starch content, beta-glucan, and phytic acid were then determined. Residual starch and beta-glucan in the DDGS are summarized in the Table 6 (Residual starch and beta-glucan content in DDGS). It can be seen that conventional process resulted in less than 1% residual starch, while STARGENT™ process resulted in 2.5% residual starch, indicating excellent conversion of the starch during SSF.

The beta-glucan content in the hulled barley is 3.90% and the residual beta-glucan level after SSF is between 0.3-0.4%. In other words, more than 95% beta-glucan was hydrolyzed resulting in DDGS with very low level of beta-glucan.

TABLE 6

Residual starch and beta-glucan content in DDGS

|  | Residual Starch % | beta-glucan % |
|---|---|---|
| STARGEN™ Process | 2.51 | 0.37 |
| Conventional Process | 0.96 | 0.39 |

Dry grind fermentation of corn normally results in DDGS containing high level of phytic acid which is undesirable from animal feed formulation point of view because the phosphate present in the phytate is unavailable due to the limited digestibility by monogastric animals. Therefore, a significant amount of phosphorus disposed to soil from the unused phytate carried out in the manure has been a concern in some countries due to pollution of the environment from animal waste, especially from swine and poultry. Interestingly in the barley STARGEN™ process, due to the hydrolysis of phytic acid, presumably by endogenous barley phytase during the viscosity reduction step at 57° C. for 1.5 hours, the resulting DDGS from yeast fermentation is essentially free from phytic acid (The phytic acid in the hulled barley samples was 0.36%). Therefore, the barley STARGEN™ process is able to produce DDGS with reduced beta-glucan and no phytic acid.

Advantages of using non-starch hydrolyzing enzymes and STARGEN™ enzyme technology for barley fermentation are clearly demonstrated: more ethanol yield, DDGS containing reduced beta-glucan and no phytic acid, elimination of jet cooking with fewer steps, less capital equipment, and less energy. Meanwhile, low concentrations of fermentable sugars in the fermenter results in enhancing the active yeast population and, along with the low pH of the SSF, limits the growth of undesirable contaminating microorganisms. These results show that use of STARGEN™ enzymes together with non-starch viscosity reducing enzymes allow ethanol producers more tools which will help in processing grains slurries to ethanol while increasing total plant yield and throughput.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of hydrolyzing starch from milled plant material, comprising:
    contacting a slurry of milled plant material with an enzyme combination of a glucoamylase, a beta-glucanase and a microbial alpha-amylase at a temperature below the initial gelatinization temperature of the granular starch in the milled plant material to obtain fermentable sugars, wherein the milled plant material comprises an endogenous phytase; and
    fermenting the fermentable sugars in the presence of microorganisms to end products comprising DDGS, wherein the DDGS are essentially free of phytic acid and essentially free of β glucan.

2. The method of claim 1, wherein the temperatures below the initial gelatinization temperature is from about 25° C. and about 77° C.

3. The method of claim 1, wherein the temperatures below the initial gelatinization temperature is from about 50° C. and about 80° C.

4. The method of claim 1, wherein the DDGS are used as an animal feed.

5. The method of claim 1, wherein the milled plant material is barley, wheat or rye.

6. The method of claim 1, wherein the enzyme composition further comprises at least one secondary enzyme selected from: a second glucoamylase, a second alpha amylase, a cellulase, a hemicellulase, a xylanase, a protease, a pullulanase, a lipase, a cutinase, a pectinase, a second beta-glucanase, a cyclodextrin transglycosyltransferase, a beta-amylase, and combinations thereof.

7. The method of claim 1, wherein the pH of the slurry is between about pH 3 and about pH 7.

8. The method of claim 1, wherein the slurry is held in contact with the enzyme composition for a period of about 2 hours to about 240 hours.

9. The method of claim 1, wherein the enzyme combination is a blend.

10. The method of claim 1, wherein the enzyme combination is not a blend.

11. The method of claim 1, wherein the milled plant material includes barley, milo, corn or combinations thereof and the contacting and fermenting steps are conducted simultaneously at a pH range of about 3.5 to about 5.5, a temperature range of about 30-about 45° C. and for a period of time of about 48 to about 90 hours, wherein at least about 50% of the starch is solubilized.

12. The method of claim 1, wherein the end products further comprise ethanol and the yield of ethanol is greater than about 8%.

13. A method of fermenting ethanol from milled plant material, comprising:
    contacting a slurry of milled plant material with an enzyme combination of a glucoamylase, a beta-glucanase and a microbial alpha-amylase at a temperature below the initial gelatinization temperature of the granular starch in the milled plant material to obtain fermentable sugars, wherein the milled plant material comprises an endogenous phytase; and
    fermenting the fermentable sugars to end products comprising DDGS and ethanol in the presence of fermenting microorganisms, wherein the DDGS have reduced phytic acid and reduced β-glucan.

14. The method of claim 13, wherein the DDGS are used for an animal feed.

15. The method of claim 13 wherein the the yield of ethanol is greater than about 8%.

* * * * *